United States Patent [19]

Pars

[11] Patent Number: 5,498,419
[45] Date of Patent: Mar. 12, 1996

[54] FUMARATE SALT OF 4-(DIETHYL-3-(1-METHYLOCTYL)-7,8,9,10-TETRAHYDRO-6,6,9-TRIMETHYL-6H-DIBENZO[B,D]PYRAN-1-OL, 4-(DIETHYL-AMINO) BUTYRIC

[76] Inventor: Harry G. Pars, P.O. Box 541, Concord, Mass. 02741

[21] Appl. No.: 253,849

[22] Filed: Jun. 3, 1994

[51] Int. Cl.$^6$ ............................... A61F 13/00; A61K 9/14
[52] U.S. Cl. ........................ 424/449; 424/427; 424/489; 514/455; 514/912; 514/913; 549/359
[58] Field of Search ........................... 549/359; 514/455, 514/913; 424/448, 449, 427, 489

[56] References Cited

U.S. PATENT DOCUMENTS

| | | | |
|---|---|---|---|
| 2,419,934 | 5/1947 | Adams | 260/333 |
| 2,419,935 | 5/1947 | Adams | 260/333 |
| 2,419,936 | 5/1947 | Adams | 260/333 |
| 2,509,387 | 5/1950 | Adams | 260/333 |
| 3,325,490 | 6/1967 | Bolger et al. | 260/247.2 |
| 3,429,889 | 2/1969 | Shulgin et al. | 260/295 |
| 3,522,260 | 7/1970 | Shulgin et al. | 260/294.3 |
| 3,632,595 | 1/1972 | Pars et al. | 260/297 |
| 3,635,993 | 1/1972 | Pars et al. | 260/297 |
| 3,728,360 | 4/1973 | Pars et al. | 260/345.2 |
| 3,856,820 | 12/1974 | Loev | 260/345.3 |
| 3,856,821 | 12/1974 | Loev | 260/345.3 |
| 3,856,822 | 12/1974 | Bender et al. | 260/345.3 |
| 3,864,492 | 2/1975 | Fager et al. | 424/283 |
| 3,873,576 | 3/1975 | Petrzilka | 260/345.3 |
| 3,886,184 | 5/1975 | Matsumoto et al. | 260/345.3 |
| 3,901,925 | 8/1975 | Devlin et al. | 260/345.3 |
| 3,927,036 | 12/1975 | Lee | 260/345.3 |
| 3,928,598 | 12/1975 | Archer | 424/283 |
| 3,944,673 | 3/1976 | Archer | 424/283 |
| 3,953,603 | 4/1976 | Archer | 424/283 |
| 3,961,057 | 6/1976 | Brown et al. | 424/248 |
| 3,984,546 | 10/1976 | Brown et al. | 424/248 |
| 3,987,188 | 10/1976 | Archer | 424/283 |
| 4,025,536 | 5/1977 | Korte et al. | 260/345.3 |
| 4,029,665 | 6/1977 | Winn | 260/293.53 |
| 4,032,540 | 6/1977 | Eder et al. | 260/340.5 |
| 4,049,653 | 9/1977 | Winn | 544/150 |
| 4,054,582 | 10/1977 | Blanchard et al. | 260/345.3 |
| 4,087,545 | 5/1978 | Archer et al. | 424/283 |
| 4,087,546 | 5/1978 | Archer et al. | 424/283 |
| 4,087,547 | 5/1978 | Archer et al. | 424/283 |
| 4,126,694 | 11/1978 | Razdan et al. | 424/283 |
| 4,126,695 | 11/1978 | Razdan et al. | 424/283 |

OTHER PUBLICATIONS

H. G. Pars et al., "Potential Therapeutic Agents Derived from the Cannabinoid Nucleus", *Advances in Drug Research*, vol. 11, 97–188 (Academic Press 1977).
K. Green et al., *Exp. Eye Res.*, 25:465–471 (1977).
R. Razdan, *Pharmacological Reviews*, 38(2):75–149 (1986).
P. Weber et al., "Lowering of Intraocular Pressure in Normotensive Human Volunteers by Naboctate", ARVO 1981, abstract No. 3, p. 196. Supplement to Investigative Ophthalmology and Visual Science, vol. 20, No. 3, Mar. 1981.

*Primary Examiner*—Jyothsna Venkat

[57] ABSTRACT

The present invention provides the fumarate salt of 4-(diethyl-3-(1-methyloctyl)-7,8,9,10-tetrahydro-6,6,9-trimethyl-6H-dibenzo[b,d]pyran-1-ol, 4-diethyl-amino)butyric acid ester, i.e. the compound having the following structure (I):

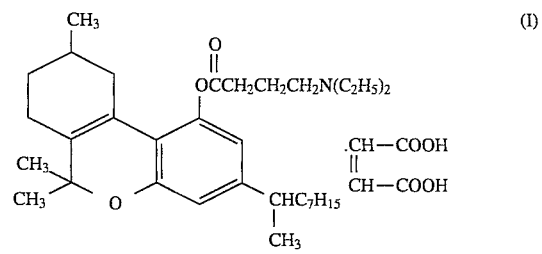

and methods of treatment, particularly treatment of glaucoma, and pharmaceutical compositions that utilize or comprise the fumarate salt (I).

14 Claims, No Drawings

FUMARATE SALT OF 4-(DIETHYL-3-(1-METHYLOCTYL)-7,8,9,10-TETRAHYDRO-6,6,9-TRIMETHYL-6H-DIBENZO[B,D] PYRAN-1-OL, 4-(DIETHYL-AMINO) BUTYRIC

BACKGROUND OF THE INVENTION

This invention is directed to the fumarate salt of 4-(diethyl-3-(1-methyloctyl)-7,8,9,10-tetrahydro-6,6,9-trimethyl-6H-dibenzo[b,d]pyran-1-ol, 4-diethyl-amino)butyric acid ester, referred to in this disclosure as HGP-2 fumarate.

The hydrochloride salt of 4-(diethyl-3-(1-methyloctyl)-7, 8,9,10-tetrahydro-6,6,9-trimethyl-6 H-dibenzo[b,d]pyran-1-ol, 4-diethylamino)butyric acid ester (HGP-2 hydrochloride), and its use as a potential antiglaucoma agent, have been reported. See naboctate hydrochloride or simply naboctate in *Pharmacological Reviews*, 38(2):75–149 (1986).

However, salts of 4-(diethyl-3-(1 -methyloctyl)-7,8,9,10 -tetrahydro-6,6,9-trimethyl-6H-dibenzo[b,d]pyran-1-ol, 4-diethylamino)butyric acid ester have been found to be unstable and therefore generally unsuitable for pharmaceutical uses. In particular, HGP-2 hydrochloride is a highly hygroscopic amorphous semi-solid, quite unstable and requires special treatment such as storage in a desiccator to prevent rapid decomposition. Accordingly, the compound is generally unsuitable for use as a pharmaceutical agent.

Glaucoma represents a significant health problem with estimates that between 2 to 9 percent of the adult population worldwide suffers from increased intraocular pressure. Current therapy include use of so-called "beta-blockers". These drugs however are not effective for all patients and often result in undesirable side effects that include lowered pulse rate, asthma and gastrointestinal problems.

It thus would be desirable to have a new means for treatment of glaucoma.

SUMMARY OF THE INVENTION

The present invention provides the fumarate salt of 4-(diethyl-3-(1 -methyloctyl)-7,8,9,10-tetrahydro-6,6,9-trimethyl-6H-dibenzo[b,d]pyran-1-ol, 4-diethyl-amino)butyric acid ester, referred to herein as HGP-2 fumarate and having the following structure (I):

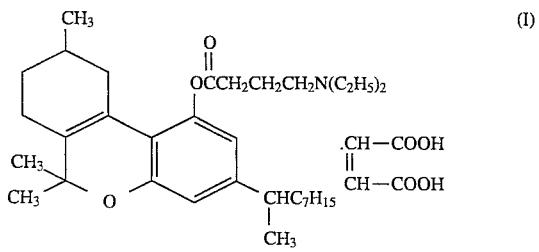

It has been most surprisingly found that HGP-2 fumarate, unlike HGP-2 hydrochloride and other salts, is a highly stable, substantially non-hygroscopic, crystalline material that shows no significant signs of decomposition over prolonged periods of storage at room temperature in open air, even periods of from 12 to 36 months or more. It has thus been found that HGP-2 fumarate is well suited for use as a pharmaceutical agent.

It also has been found that HGP-2 fumarate is useful for treatment of glaucoma. Accordingly, the present invention includes methods for treatment and/or prophylaxis of glaucoma. The methods of invention in general comprise administration of a therapeutically effective amount of HGP-2 fumarate to a mammal, particularly a human.

The invention also provides pharmaceutical compositions comprising a therapeutically effective amount of HGP-2 fumarate and a pharmaceutically acceptable carrier.

The present invention includes both racemic mixtures and optically enriched mixtures of HGP-2 fumarate. An optically enriched mixture contains substantially more (e.g. about 60%, 70%, 80% or 90% or more) of one enantiomer or diastereoisomer than the other stereoisomer(s).

Other aspects of the invention are disclosed infra.

DETAILED DESCRIPTION OF THE INVENTION

HGP-2 fumarate may be suitably prepared as described in Example 1 which follows and which includes preparation of the HGP-2 free base and then formation of a fumarate salt thereof, or by other suitable route. Optically enriched mixtures of HGP-2 fumarate can also be prepared by the general procedure described in Example 1 below by making appropriate modifications to render the synthesis enantioselective. For example, an optically active 3-methylcyclohexanone (either the (R) or (S) isomer) can be employed (see Step 5 of Example 1 below) to introduce an optical active carbon to the ring structure of HGP-2 fumarate, i.e., so that optically active HGP-2 fumarate is provided wherein the chiral ring carbon is selectively either of the (R) or (S) configuration, and that HGP-2 fumarate is substantially free of stereoisomer(s) having alternate configuration at the chiral ring carbon. Optically active HGP-2 fumarate where the chiral 1-octyl carbon atom is selectively either of the (R) or (S) configuration (i.e., HGP-2 fumarate substantially free of stereoisomer(s) having alternate configuration at the chiral 1-octyl carbon atom) can be prepared by e.g. employing an enantioselective alkylation of the 3,5-dimethoxyacetophenone or, alternatively, separation of the (R) and (S) enantiomers of 2-(3',5'-dimethoxyphenyl)-2-octanol such as by column chromatography using an optically active binding material as is known in the art. Substantial separation of stereoisomers of HGP-2 fumarate having either an (R) or (S) ring carbon also could be accomplished by use of such a column having optically active binding material. Designations herein of stereoisomers having the (R) or (S) configuration(s) are in accordance with the Cahn-Ingold-Prelog nomenclature system. See Carey, F. A., *Advanced Organic Chemistry*, Part A, p. 65–66 (2d ed., Plenum Press 1984).

As discussed above, the invention provides methods for treatment and/or prophylaxis of glaucoma, including chronic open-angle glaucoma, acute angle-closure glaucoma and corticosteroid-induced glaucoma.

It has been found that HGP-2 fumarate exhibits a significant and prolonged reduction of intraocular pressure. For example, administration of a single drop of an aqueous treatment solution containing 0.5% w/w HGP-2 fumarate as the active agent to the eye of test subjects (rabbits) produced a significant and prolonged (up to about 5 hours) lowering of intraocular pressure relative to control subjects that did not receive HGP-2 fumarate.

It also has been found that administration of a single 3.5 mg oral (capsule) dose of HGP-2 fumarate to each of twenty human subjects resulted in a reduction of intraocular pressure (IOP) of between about 30 to 50 percent, relative to pre-administration IOP levels, for a minimum of about 8 to 12 hours for each subject.

While HGP-2 fumarate may be administered alone to a patient, the compound also may be used as part of a pharmaceutical composition. Pharmaceutical compositions of the invention in general comprise HGP-2 fumarate together with one or more acceptable carriers. The carriers must be "acceptable" in the sense of being compatible with other ingredients of the formulation and not deleterious to the recipient thereof.

Compositions of the invention may also include, in addition to HGP-2 fumarate, one or more other active medicaments. For example, for treatment of glaucoma, a composition may be administered to a subject that contains HGP-2 fumarate together with other therapeutic agents used for the treatment of glaucoma such as timolol, pilocarpine, betaxolol and the like.

Pharmaceutical compositions of the invention include those for oral, rectal, nasal, topical (including transdermal, eye drops, buccal and sublingual), vaginal, or parenteral (including subcutaneous, intramuscular, intravenous and intradermal) administration. Generally preferred are oral and topical administration, particularly by eye drop or transdermal applications.

The pharmaceutical compositions of the invention may be presented in unit dosage form, e.g., tablets and sustained release capsules, and in liposomes and may be prepared by any methods well known in the art of pharmacy. Such methods include the step of bringing into association the to be administered ingredients with the carrier. In general, the compositions are prepared by uniformly and intimately bringing into association the active ingredients with liquid carriers, liposomes or finely divided solid carriers or both, and then if necessary shaping the product.

Compositions of the invention suitable for oral administration may be presented as discrete units such as capsules, cachets or tablets each containing a predetermined amount of the active ingredient; as a powder or granules; as a solution or a suspension in an aqueous liquid or non-aqueous liquid; packed in liposomes, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, dispersing agent, etc. Molded tablets may be made by molding in a suitable machine a mixture of the powdered compound moistened with an inert liquid diluent. The tablets may optionally be coated or scored any may be formulated so as to provide slow or controlled release of the active ingredient therein.

Capsules can be made by procedures known in the art, e.g., by admixing HGP-2 fumarate with one or more suitable carriers that could include e.g. a light mineral oil, granulating the mixture and then filling gelatin capsules with the granulated product to provide a uniform dose per capsule.

Compositions suitable for topical administration to the skin may be presented as ointments, creams, gels and pastes containing HGP-2 fumarate and a pharmaceutically acceptable carrier. A preferred composition for application directly to an eye of a patient comprises HGP-2 fumarate in an amount of from about 0.001 to 2 % w/w in an aqueous or non-aqueous (e.g. an oil such as a mineral oil) solution or suspension. Such treatment compositions may be suitably administered directly to the eye of the patient in form of drops.

A further preferred topical delivery system is a transdermal patch containing the ingredient to be administered. Typically a transdermal patch delivery system of the invention will contain between about 5 and 20 milligrams of HGP-2 fumarate within the patch matrix. Transdermal patch systems known in the art will be suitable for purposes of the present invention including a multilayer patch that comprises, in successive order, a backing layer, a drug reservoir layer that contains the HGP-2 fumarate prior to use, an optional membrane layer and an adhesive layer for affixing the drug delivery device to the skin of a patient.

Other compositions suitable for topical administration include lozenges, typically comprising the ingredients in a flavored basis.

Compositions suitable for parenteral administration include aqueous and non-aqueous sterile injection solutions which may contain anti-oxidants, buffers, bacteriostats and solutes which render the formulation isotonic with the blood the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It will be appreciated that the actual preferred amount of HGP-2 fumarate used in a given therapy will vary according to a number of factors as will be recognized by the attendant physician such as the patient's weight, general health, sex, etc., the particular indication being treated, the particular composition formulated, the mode of application, the selected site of administration, etc. Optimal administration rates for a given protocol of administration can be readily ascertained by those skilled in the art using conventional dosage determination tests conducted with regard to the foregoing guidelines.

In general, a suitable effective dose of HGP-2 fumarate will be in the range of from about 0.01 to 50 milligrams per kilogram of recipient per day, preferably in the range of from about 0.1 to 20 milligrams per kilogram of recipient per day. The desired dose is suitably administered once daily, or more preferably several sub-doses, for example, 2 to 4 sub-doses administered at appropriate intervals through the day, or other appropriate schedule. Such sub-doses may be administered as unit dosage forms, e.g., containing from 0.05 to 10 milligrams of HGP-2 fumarate per unit dosage. For an oral administration such as by capsules or tablets, the drug preferably will be administered no more than 1 to 3 times daily in an amount of about 0.1 to 5 milligrams of HGP-2 fumarate per unit dosage, more preferably about 0.5 to 5 milligrams of HGP-2 fumarate per unit dosage. In particular, unit dosages of HGP-2 fumarate of 3.5 mg, 2.5 mg and 1.5 mg for oral administration should be useful.

All documents mentioned herein are incorporated herein by reference.

The present invention is further illustrated by the following examples. These examples are provided to aid in the understanding of the invention and are not to be construed as limitations thereof.

EXAMPLE 1

Synthesis of Fumarate Salt of 4-(Diethyl-3-(1-methyloctyl)-7,8,9,10-tetrahydro-6,6,9-trimethyl-6H-dibenzo[b,d]pyran-1-ol, 4-diethyl-amino)butyric Acid Ester (HGP-2 fumarate)

HGP-2 fumarate is suitably prepared in accordance with the following Scheme I and Steps 1 through 7a. In Steps 1 through 7a, references made to 1, 2, 3, 4, 5, 6, 7, 8, 9, 10, 11, 13 and 14 refer to the corresponding compounds depicted in Scheme I.

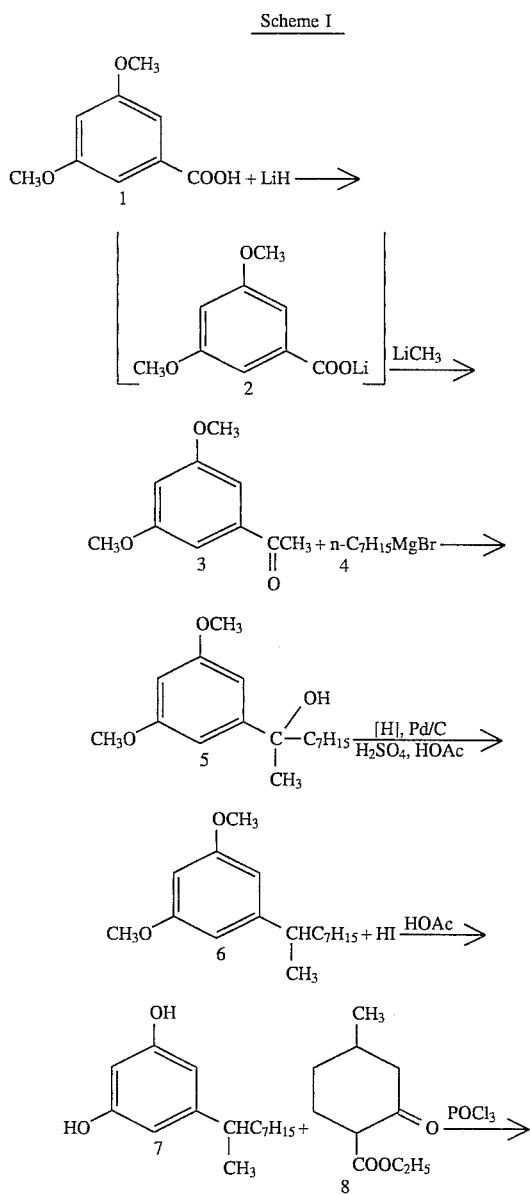

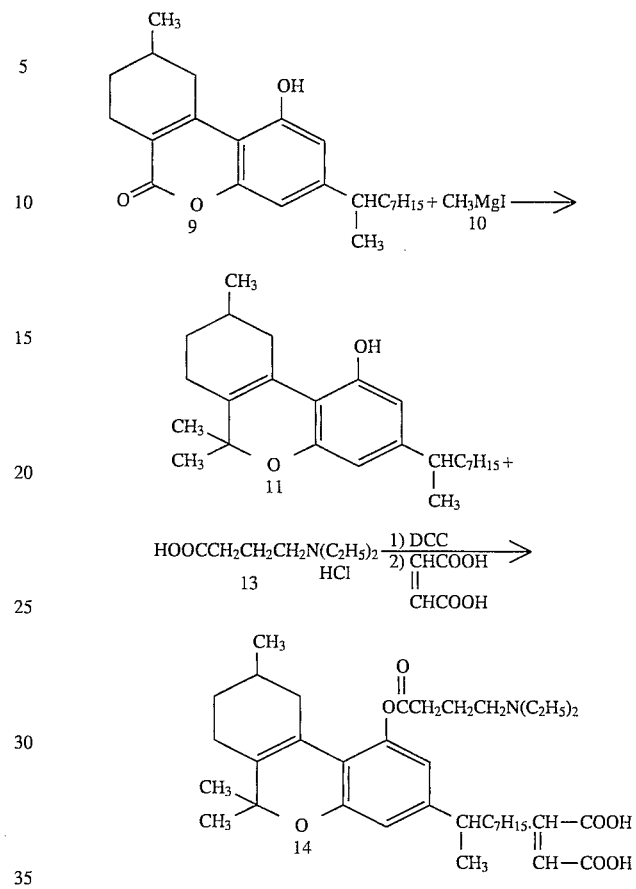

Step 1. Synthesis of 3,5-Dimethoxyacetophenone (3)

The lithium salt (2) of 3,5-dimethoxybenzoic acid was prepared from 136.0 g (0.747 mol) of the acid (m.p. 178°–183° C.; recrystallized from ethyl acetate) and 12.3 g (1.547 moles) of lithium hydride (Ventron) by adding the solid acid, in portions through a Gooch tubing, to a slurry of the hydride in 1280 ml of dry tetrahydrofuran (THF). A strong mechanical stirrer was needed to keep the reaction mixture in motion as it thickened. The addition was made at room temperature and the rate of addition was determined by the vigor of hydrogen evolution. Thirty minutes after the end of the addition, the reaction mixture was heated slowly to 60°–62° C. and held there until evolution of hydrogen had stopped, at least 3 hours.

The reaction mixture was cooled to 5° C. and 0.786 mol of methyllithium (as a solution in diethyl ether; 500 ml of 1.3 molar and 85 ml of 1.6 molar; Ventron) was added during 0.5 hour. The reaction was completed (as indicated by thin layer chromatography (TLC)) by stirring for 0.5 hour at 5° C. and then for 1 hour at room temperature. The reaction mixture was poured slowly into a mixture of 250 ml of concentrated hydrochloric acid in ice, with vigorous stirring to assure complete and rapid mixing, and ice was added as needed to keep the solution cold. The ketone 3 was recovered from the washed- (water and aqueous sodium carbonate) and dried-ether layer after removal of the solvent in a rotary evaporator. The yield of 3 was 131.5 g (97%) as a light yellow solid showing essentially a single spot on TLC (1:2 ethyl acetate/hexane, $R_f$=0.39). It was used in the next step without further purification. It can be recrystallized from petroleum ether as a cream-colored solid, m.p. 39°–41° C. This agrees with the published m.p. The NMR Spectrum is consistent with the proposed structure.

Step 2. Synthesis of 2-(3',5'-dimethoxyphenol)-2-octanol (5)

The ketone 3 was converted to the alcohol 5 in practically quantitative yield by reaction with the Grignard reagent 4. Thus, a solution of 131.5 g (0.73 mol) of 3,5-dimethoxyacetophenone (3) in 175 ml of anhydrous diethyl ether was added during 25 minutes to a solution of the Grignard reagent, prepared in the normal way from 198.4 g (1.108 mols) of 1-bromoheptane (Aldrich) and 24.5 g (1.008 mols) of magnesium shavings, in 940 ml of anhydrous diethyl ether. The initial temperature of the reaction mixture was 5° C. and the maximum temperature was 18° C. The cooling bath was removed at the end of the addition and the reaction mixture was heated at reflux for 30 minutes. By TLC (1:2 ethyl acetate/hexane, $R_f$=0.47) there was no unreacted ketone at this point.

The cooled reaction mixture was poured in a thin stream into a vigorously stirred slurry of ice, solid ammonium chloride and 75 ml of concentrated hydrochloric acid. The alcohol 5 was recovered from the washed and dried ether layer upon concentration in a rotary evaporator. The dark yellow oil (221.5 g) also contained the excess bromoheptane (17.9 g). The product showed two spots on TLC, the minor one being slower moving, but it was used in the next step without further purification.

Step 3. Synthesis of 2-(3',5'-dimethoxyphenyl)nonane (6)

Hydrogenolysis of the alcohol 5 was carried out in a Parr apparatus at room temperature and initial pressure of about 50 psig. The crude alcohol 5 (221.5 g; 0.72 mol) was dissolved in 677 ml of glacial acetic acid, and 5 ml of concentrated sulfuric acid (yellow solution turned red) and 25 g of 5% palladium-on-charcoal were added. Reduction was complete in slightly more than 2 hours, when TLC showed the alcohol had all reacted. The catalyst was removed by suction filtration of the yellow reaction mixture through a pad of Celite and the filter cake was washed with glacial acetic acid. The brown oily residue remaining from concentration of the filtrate in a rotary evaporator was taken up in water and 1:1 diethyl ether/petroleum ether. The lower aqueous layer was extracted with diethyl ether and discarded. The acid was washed out of the combined organic layers with sodium bicarbonate, and the yellow organic phase was washed to neutrality, dried, and concentrated in a rotary evaporator. The residue of crude ether 6, (195.5 g) was fractionally distilled at reduced pressure, to give 149.5 g (77% from the ketone 3) of the nonane 6, as a colorless liquid, b.p. 114°–120° C./0.2 mm. TLC showed the forerun (22.3 g, b.p. 44°–113° C./0.2 mm) contained additional amounts of 6. Three very minor spots were faintly visible by TLC (1:4 ethyl acetate/hexane) of the main fraction, along with the major one for 6 at $R_f$=0.58. Retention time on GLC was 4.69 minutes (2% OV-17, column 190° C.). NMR Spectra were consistent with the proposed structure.

Step 4. 5-(1'-Methyloctyl)resorcinol (7)

The ether 6 was demethylated by heating with strong hydriodic acid in acetic acid. To a solution of 149 g (0.564 mol) of 2-(3',5'-dimethoxy)nonane (6) (b.p. 114°–128° C./0.2 mm) in 317 ml of hydriodic acid (Fisher, 55% HI, d=1.7), contained in a 3-neck round-bottom flask carrying a short Vigreux column and condenser set for downward distillation, was carefully added 317 ml of acetic anhydride with mechanical stirring. The temperature was allowed to rise in the exothermic reaction. Iodomethane was then removed (vapor temperature 55° C.); from time to time additional acetic anhydride (total 317 ml) was added whenever the rate of distillation slowed. After 2.5 hours the pot temperature had risen to 115° C. and distillation had stopped. The temperature was raised until the vapor reached 112° C. Dilution of the combined distillate with water caused separate of 62 ml of iodomethane (88% of theory).

Acetic acid was stripped from the residue by vacuum distillation (sodium sulfite and water were added to assist in removal of color and acid), and the remainder was partioned between water and 1:1 diethyl ether/benzene. Additional color and acid were removed from the organic phase by washing with aqueous solutions of sodium sulfite and sodium bicarbonate. Then a wash with dilute hydrochloric acid followed by water to neutrality, and drying, left a dark green solution, which was concentrated in a rotary evaporator. Vacuum distillation of the dark red residue gave 105.8 g (79%) of the resorcinol 7 as a viscous orange oil, b.p. 175°–185° C./0.3 mm; showing a major spot on TLC (1:2 ethyl acetate/hexane, $R_f$=0.28), along with a number of minor spots from unidentified impurities. The resorcinol showed retention time of 3.41 minutes of GLC (2% OV-17, column 220° C.). NMR spectra were in agreement with its proposed structure, and with published data.

Step 5. Synthesis of 9-methyl-3-(1'-methyloctyl)-6-oxo-7,8,9,10 -tetrahydro-6H-dibenzo(b,d)pyran-1-ol (9)

This Pechamann reaction was most successful when the time of reaction was not prolonged and the temperature was kept moderate. A solution of 105.8 g (0.448 mol) of 5-(1'-methyloctyl) resorcinol (7) and 94.8 g (0.515 mol) of ethyl 4-methyl-2-cyclohexanone-1-carboxylate (8; Aldrich) in 525 ml of benzene was made in a flask under a nitrogen atmosphere and protected from moisture by a drying tube, and 82.3 g (0.537 mol) of phosphorus oxychloride (Baker Analyzed Reagent) was added with good magnetic stirring. The golden yellow reaction mixture was stirred 50 minutes at room temperature, then kept for 30 minutes in an oil bath at 70°–75° C. After cooling and standing overnight at room temperature, the cherry red reaction mixture (TLC showed the absence of starting materials) was poured carefully into an ice-water mixture with vigorous mechanical stirring. Stirring was continued until the solid orange precipitate initially formed had changed to a creamy, tan emulsion (2.5 hours). Much of the water was decanted. The thick emulsion was collected by suction filtration, washed well with cold hexane and air dried. Drying was complete in a vacuum oven, over phosphorus pentoxide and potassium hydroxide.

The yield of dibenzopyranol 9 was 131.3 g (82%) as a tan solid, m.p. 136°–138.5° C. (capillary). Published data: (138.0° C.). It could be recrystallized from benzene (3 ml/g) by the addition of a half-volume of hexane, but the m.p. was not improved. TLC showed essentially a single spot (1:2 ethyl acetate/hexane, $R_f$=0.50), and on GLC (2% OV-17, column 295° C.) the retention time (silylated sample) was 3.40 minutes.

Step 6. Synthesis of 3-(1'-Methyloctyl)-7,8,9,10-tetrahydro-6,6,9 -trimethyl-6H-dibenzo(b,d)pyran-1-ol (11)

A solution of 131.3 g (0.368 mol) of 9-methyl-3-(1'-methyloctyl)-6 -oxo-7,8,9,10-tetrahydro-6H-dibenzo(b,d)pyran-1-ol (9) in 450 ml of dry, distilled tetrahydrofuran was added dropwise to a well-stirred solution of Grignard reagent, made in the usual manner from 44.7 g (1.84 mols) of magnesium shavings and 287.4 g (2.025 mols) of iodomethane (Aldrich), in 127 ml of anhydrous diethyl ether. During the addition, more diethyl ether (1050 ml) was added without much effect, in an effort to enhance the fluidity of the very thick reaction mixture. The reaction was completed by heating at reflux for 1.5 hours and standing at room temperature for 72 hours.

The reaction mixture was poured into a well-stirred mixture of ice, water, and hydrochloric acid, and the product was isolated from the washed and dried ether solution in the usual manner. Closure of the pyran ring to form 11 was completed by adding 2 ml of concentrated hydrochloric acid to the dark red concentrate when it had reached a volume of about 500 ml, and heating it for 15 minutes in a water bath at about 50° C. Dilution with water, followed by washing, drying and concentrating of the organic layer left 138.8 g of crude pyran 11 showing a major spot on TLC at $R_f$=0.52 (1:4 ethyl acetate/hexane).

The pyran was easily purified by column chromatography through silica gel 60 (70–230 mesh), loading ratio 10:1, eluant 2:98 ethyl acetate/hexane. The product consisted of 116.4 g (85%) of 11 as a dark red, very viscous oil, showing a single spot on TLC. The retention time of a silylated sample on GLC was 4.00 minutes (2% OV-17, column 260° C.). A second peak with retention time 4.75 minutes was attributed to the presence of the isomeric pyran, in which the double bond of the cyclohexane ring was between carbon atoms 10 and 10a; it amounted to 10% of the chromatographed product.

Step 7. Synthesis of 4-(diethyl-3-(1-methyloctyl)-7,8,9,10-tetrahydro-6,6,9 -trimethyl-6H-dibenzo[b,d]pyran-1-ol, 4-diethyl-amino)butyric acid ester ● Fumarate (14)

To a solution of 20.68 g (0.0558 mol) of 3-(1'-methyloctyl)-7,8,9,10-tetrahydro-6,6,9 -trimethyl-6H-dibenzo(b,d)pyran-1-ol (11) and 11.46 g (0.0586 mol) of 4-(diethylamino)butyric acid hydrochloride 13 (prepared as described in Step 7a below, having m.p. 167°–168.5° C., and dried for 2 hours at 60° C. over potassium hydroxide pellets in a vacuum oven prior to use) in 200 ml of dry dichloromethane (distilled over $P_2O_5$) was added 12.088 g (0.0586 mol) of dicyclohexylcarbodiimide (DCC; Aldrich 99%) and washed in with 50 ml of additional dry dichloromethane. The solution was stirred (magnetic) at 19°–20° C. for 16 hours. TLC in 10% MeOH/chloroform showed the disappearance of pyranol; the reaction was now complete. The reaction mixture was cooled in an ice bath for 1.5 hours, filtered through a Buchner funnel and the precipitated dicyclohexylurea was washed with 50 ml of dichloromethane. The combined filtrate was washed with saturated sodium bicarbonate solution followed by saturated brine and then with 50 ml of water. After drying (magnesium sulfate) 1.0 g of decolorizing carbon was added and the mixture was filtered through a celite bed. The cake was washed with dichloromethane and the solvent was evaporated on a rotary evaporator. After pumping on the residue at 1 mm for about 1 hour, 200 ml of distilled hexane was added. The solution was left in the freezer (−5° C.) for 48 hours. It was filtered through a sintered funnel with a celite bed. After washing the cake with hexane, the hexane was removed on a rotary evaporator and the residue was left over a high vacuum pump (0.6 mm/Hg) overnight to remove any residual volatile material. It gave 28.0 g (98% yield) of a viscous liquid (pinkish). It was pure by C,H,N elemental analysis; TLC showed a single spot $R_f$=0.27 (silica, 10:90 ethanol/chloroform). By HPLC analysis (92%) isooctane, 8% ethanol containing 1% $NH_4OH$) it was >99% pure. NMR and IR spectra were also consistent with proposed structure.

A combined sample of the HGP-2 free base was then converted to the fumarate salt (14). Fumaric acid (8.23 g, 0.071 mol) was dissolved in tetrahydrofuran (200 ml) and added to a solution of HGP-2 free base (36.3 g, 0.071 mol) in tetrahydrofuran (100 ml). The flasks were then rinsed with additional tetrahydrofuran (50 ml) to ensure complete material transfer.

The reaction mixture was brought to reflux for 15 minutes. Tetrahydrofuran was then removed on a rotary evaporator and the residue dried at 1 mm Hg for a few minutes. Dry ether (250 ml) was then added and a few seed crystals introduced. A precipitate began to appear and the solution was stored in a refrigerator overnight.

The solid was then filtered through a Buchner funnel, washed with ether and minimal petroleum ether. The solid was redissolved in dry THF as before and the procedure was repeated. The solid was dried at 60° C./1 mm Hg for 4 hours to provide 40 g of the title compound, HGP-2 fumarate, as a white solid, m.p. 114°–115° C.

Step 7a: Synthesis of 4-(Diethylamino) butyric acid hydrochloride (13)

4-diethylamino butyric acid hydrochloride (13) was prepared as generally described by Blicke et al., *J. Amer. Chem. Soc.*, 63:2488 (1941). Thus, a mixture of 4.8 g (0.035 mol) of methyl γ-chlorobutyrate, 8.0 g (0.053 mol) of sodium iodide and 30 ml of acetone was refluxed for 8 hours. The acetone was removed, the residue extracted with ether and the ether extract shaken with sodium thiosulfate solution. The ether layer was dried over fused $Na_2SO_4$ and the solvent removed to provide 4.6 g of methyl γ-iodobutyrate, b.p. 80°–83° C. (11 mm).

To 4.6 g of the thus formed methyl γ-iodobutyrate was added 30 ml of benzene and five grams of diethylamine. The mixture was heated in a Wheaton bottle for 3 hours at 60° C. The precipitated diethylamino hydriodide was filtered off. From the filtrate there was obtained 2.6 g (74%) of methyl γ-diethylamino butyrate, b.p. 61°–63° C. (3 mm Hg).

The thus formed methyl γ-diethylamino butyrate was heated for 1 hour on a steam bath with three times its volume of 18% HCl and the mixture was then concentrated until crystals began to appear. Acetone was added and the precipitated γ-diethylaminobutyric acid hydrochloride was recrystallized from a mixture of alcohol and ether, m.p. 166° C. (calc. yield 2.9 g).

EXAMPLE 2

1. Materials 1.1 HGP-2 fumarate

The HGP-2 fumarate (14 in Scheme I) was stored at room temperature in a desiccator prior to use.

1.2 Test Solutions

Solutions were prepared in advance and stored in the refrigerator for the duration of each crossover experiment. Administered solutions containing HGP-2 fumarate were made by carefully weighing a precise amount of HGP-2 fumarate into a volumetric flask, adding 100 mg of mannitol and diluting to 5 ml with acetate buffer with a pH of 4.0. The solution concentration was 0.5% HGP-2 fumarate in an acetate buffer solution. Control solutions were prepared by diluting 100 mg of mannitol up to a volume of 5 ml with the same acetate buffer, pH 4.0. For both the control and HGP-2 fumarate solutions, the acetate buffer solution was prepared using 2.4 ml of glacial acetic acid, 6.6 ml 0.94M NaOH, 37.5 ml benzyl alconium chloride solution (1:750 dilution) and diluting to 500 ml with distilled water and adjusting to pH 4.0 if necessary.

1.3 Animals

Eight male New Zealand white rabbits purchased from Millbrook Farms, Amherst, Mass. Body weight of each animal ranged from 1.8 to 2.0 1 kg. Each animal was identified by tattoo. The animals were individually housed in suspended metal cages with grid bottoms. The rabbits were housed in a room equipped with air conditioning equipment set to maintain the air temperature between 60° and 75° F. and a relative humidity between 30% and 70%. Fluorescent lighting was set to an artificial cycle of 12 hours light/12 hours dark during the study period including acclimation.

All the rabbits were acclimated to the water-loading and intraocular pressure reading procedures. They were acclimated to the procedure by running a mock experiment using saline as the test solution. Rabbits were restrained in cloth bags, water-loaded with 200 ml of distilled water, and IOP measurements were made using an Alcon applanation pneumatonograph.

Prior to each measurement, the animals' eyes were anesthetized with 0.5% tetracaine hydrochloride solution (Alcon), followed by a 0.9% saline rinse. Readings were taken on the same time schedule as that which was to be used for the study.

A pelleted high fiber rabbit chow (Purina HF 5326) and a supply of fresh, potable water was available ad libitum throughout the study, including the acclimation period, with the exception that for approximately 16 hours prior to testing and during the actual text, the animals did not have access to food or water.

1.4 Applanation Pneumatonograph

An Alcon applanation pneumatonograph was used for all intraocular pressure (IOP) measurements.

Each day of the study prior to use, the pneumatonograph was switched on, allowed to "warm up", zeroed and checked against a known pressure using an Alcon calibration device.

2. Protocol Design

The study design is outlined in Table 1 below.

Animals were allocated to treatment using a random numbers table. Random allocation also determined, for unilateral administration, which eye received treatment with HGP-2 fumarate.

The study utilized a double crossover design with intervening baselines both with and between crossover. Re-randomization to treatment groups occurred prior to the start of the second crossover.

TABLE 1

TREATMENT PROTOCOL FOR DETERMINING
CONTRALATERAL EYE EFFECT OF 0.5%
HGP-2 FUMARATE

| STUDY WEEK 1 | GROUP Ia (n = 4) | GROUP IIa (n = 4) |
| --- | --- | --- |
| Day 1 | 0.05 ml vehicle, bilateral administration (crossover control eyes) | 0.05 ml of 0.5% HGP-2 fumarate, unilateral administration (treated eye) 0.05 ml of vehicle; unilateral administration (contralateral eye) |
| Day 3 | 0.05 ml of 0.5% HGP-2 fumarate, unilateral administration (treated eye) 0.05 ml of vehicle, unilateral administration (contralateral eye) | 0.05 ml vehicle, bilateral administration (crossover control eyes) |
| STUDY WEEK 2 | GROUP Ib (n = 4) | GROUP IIb (n = 4) |
| Day 8 | 0.05 ml vehicle, bilateral administration (crossover control eye) | 0.05 ml of 0.5% HGP-2 fumarate, unilateral administration (treated eye) 0.05 ml of vehicle, unilateral administration (contralateral eye) |
| Day 10 | 0.05 ml of 0.5% HGP-2 fumarate, unilateral administration (treated eye) 0.052 ml of vehicle, unilateral administration (contralateral eye) | 0.05 ml vehicle, bilateral administration (crossover control eye) |

Rabbits randomly assigned to Group Ia or IIa on Day 1: Eye (left or right) receiving HGP-2 fumarate was also randomly assigned.
Rabbits used during Week 1 were then reassigned at random, to Group Ib or IIb; the eye receiving HGP-2 fumarate was pre-determined based on Week 1 assignment, i.e., if left eye received HGP-2 during Week 1, the right eye received HGP-2 during Week 2 and vice versa.

3. Methods 3.1 Control (Base Line) Measurements

Rabbits were placed in restraining bags and allowed to settle for at least 15 minutes prior to taking the day's control intraocular pressure measurements. These readings were taken for each animal before water-loading and dosing. Two measurements were made 30 minutes apart and were averaged to get a base line (pre-treatment) reading for that day.

3.2 Water-loading and Dosing

Each animal was water-loaded with 200 ml distilled water by oral gavage using a size 8, 16" feeding tube to artificially elevate intraocular pressure. Immediately following water-loading, each rabbit was dosed with 50 μl of dosing solution (vehicle in both eyes or 0.5% HGP-2 fumarate in one eye and vehicle in the contralateral eye).

3.3 Schedule for IOP Measurements

Intraocular pressure measurements were taken for both eyes of each animal at the following post-treatment intervals: 20, 60, 120, 180, 240 and 300 minutes. At each time interval three readings were taken for each eye. An average of these three readings determined the value recorded for that time interval.

3.4 Data Presentation

The intraocular pressure (IOP) measurements were recorded as absolute pressure in mm of Hg.

Relative intraocular pressure (mm of Hg) was calculated at each post-treatment time interval as follows: IOP (pre-treatment)+IOP (Time t). A drop in pressure was assigned a negative value, a rise in pressure a positive value.

3.5 Statistical Analysis

Absolute and relative IOP values were analyzed using a pared 't' test for statistical significance. Tests were performed between the following treatment groups:

HGP-2 fumarate vs. Crossover Control (vehicle treated)

HGP-2 fumarate vs. Contralateral (vehicle treated)

Contralateral (vehicle treated) vs. Crossover Control (vehicle treated)

The null hypothesis was accepted or rejected on the basis of a two-tail test.

4. Results

The time course effects of a single unilateral instillation of 0.5% HGP-2 fumarate in the water-loaded rabbit were as follows:

1. Contralateral vs Crossover Control IOP Values (Individual Values: Tables 1a, 1b, 2a, 2b which follow).

Group Mean Values indicate that vehicle treated contralateral and crossover control eyes showed a similar response to water-loading during the first three hours post treatment: there was a sharp rise in IOP followed by a gradual decrease back to pretreatment levels. At the next two intervals (240 and 300 minutes), however, the mean IOP of the contralateral eyes continued to drop while that of the crossover control eyes increased. The difference between the relative IOP values of the two groups was significant at 240 minutes ($\Delta=3.5$ mm of Hg, $0.01<p<0.025$) and 300 minutes ($\Delta=3.2$ mm of Hg, $0.025<p<0.05$) post treatment.

2. Contralateral vs. HGP-2 fumarate IOP Values (Individual Values: Tables 1a, 1b, 2a, 2b which follow; Group Mean Values: Table 3 which follows).

Both the 0.5% HGP-2 fumarate treated eyes and the vehicle treated contralateral eyes showed a rise in mean IOP at 20 minutes post water-loading. The rise was greater, although not significantly greater ($p\approx0.1$), in the eyes which received HGP-2 fumarate. During the next three hours mean IOP dropped sharply in both groups but the decrease in the HGP-2 fumarate group was of significantly greater amplitude as recorded at 120 ($0.025<p<0.05$) and 180 ($0.005<p<0.01$) minutes.

The lowest mean relative IOP readings were taken at 180 minutes in the HGP-2 fumarate treated group ($-2.7\pm0.8$ mm Hg) and at 240 minutes in the contralateral eye group ($-1.8\pm1$ mm Hg). Group Mean Differences were not statistically significant at either 240 or 300 minutes post water-loading.

3. HGP-2 Fumarate vs Crossover Control IOP Values (Individual Values: Tables 1a, 1b, 2a, 2b which follow; Group Mean Values: Table 4 which follows).

Mean IOP increased from 0 to 20 minutes post water-loading in both groups, but was significantly higher in the HGP-2 fumarate treated eyes ($\Delta=6\%$, $0.025<p<0.05$). During the next three hours the IOP dropped in both groups, with the crossover control mean values returning to baseline level at the 180 minute measurement interval. IOP decreased below pretreatment levels in the HGP-2 fumarate group, with a maximum drop recorded at 180 minutes. Values in the treated group were significantly lower ($0.025<p<0.05$) than control group values at 120 ($\Delta=3.3$ mm Hg) and 180 ($\Delta=2.1$ mm Hg), but not at 240 or 300 minutes post treatment.

TABLE 1a

INDIVIDUAL VALUES FOR ABSOLUTE INTRAOCULAR PRESSURE, STUDY WEEK 1
Effect of Unilateral Administration of HGP-2 Fumarate (0.5%, topical instillation of 50 ul drop)
on Absolute Intraocular Pressure in the Rabbit Using the Water Load/Crossover Assay[1]

| | Absolute Intraocular Pressure (mm Hg) Rabbit No. | | | | | | | | | | | | | | | |
|---|---|---|---|---|---|---|---|---|---|---|---|---|---|---|---|---|
| | C888 | | C891 | | C892 | | C893 | | C897 | | C925 | | C926 | | C949 | |
| Time[3] | R[2] | L[2] | R | L | R | L | R | L | R | L | R | L | R | L | R | L |
| | | | | | | | Control[4] | | | | | | | | | |
| PT[6] | 25.1 | 24.5 | 24.2 | 17.8 | 20.3 | 19.9 | 27.9 | 20.5 | 19.2 | 21.7 | 20.7 | 15.8 | 25.0 | 19.9 | 23.2 | 19.5 |
| +20 | 34.5 | 35.5 | 28.8 | 30.0 | 34.3 | 27.3 | 32.7 | 33.0 | 33.0 | 35.0 | 35.8 | 31.0 | 34.3 | 25.7 | 33.7 | 31.3 |
| +60 | 21.0 | 27.3 | 40.2 | 38.7 | 31.2 | 29.8 | 35.0 | 25.0 | 24.0 | 29.8 | 23.8 | 22.2 | 34.0 | 28.3 | 29.2 | 25.0 |
| +120 | 18.5 | 26.2 | 28.2 | 24.8 | 21.0 | 20.2 | 21.2 | 15.7 | 25.2 | 25.2 | 22.3 | 17.5 | 24.5 | 20.2 | 25.8 | 18.5 |
| +180 | 13.3 | 17.3 | 22.2 | 17.7 | 20.5 | 19.7 | 20.3 | 21.0 | 23.2 | 22.7 | 22.7 | 16.0 | 21.2 | 15.8 | 19.5 | 16.7 |
| +240 | 23.0 | 17.2 | 33.2 | 24.5 | 21.7 | 18.8 | 30.3 | 24.7 | 18.5 | 24.2 | 24.7 | 18.7 | 28.7 | 11.2 | 23.2 | 20.8 |
| +300 | 19.5 | 18.3 | 31.3 | 21.8 | 22.0 | 19.2 | 23.2 | 23.0 | 20.8 | 23.0 | 24.5 | 17.0 | 23.8 | 11.3 | 24.8 | 24.8 |
| | | | | | | | Treated[5] | | | | | | | | | |
| | ★ | ♦ | ♦ | ★ | ♦ | ★ | ♦ | ★ | ♦ | ★ | ★ | ♦ | ★ | ♦ | ★ | ♦ |
| PT[6] | 30.8 | 24.1 | 27.1 | 25.0 | 19.0 | 19.3 | 25.2 | 17.1 | 21.4 | 21.8 | 18.8 | 19.1 | 24.9 | 22.7 | 23.4 | 20.6 |
| +20 | 38.7 | 34.7 | 31.5 | 31.3 | 30.8 | 27.5 | 41.0 | 28.0 | 29.5 | 22.5 | 38.8 | 34.7 | 36.8 | 35.2 | 41.3 | 38.3 |
| +60 | 33.3 | 24.8 | 31.5 | 34.2 | 22.8 | 28.8 | 29.7 | 23.2 | 21.3 | 24.0 | 25.7 | 23.7 | 36.0 | 24.5 | 24.8 | 25.2 |
| +120 | 15.7 | 16.0 | 23.8 | 29.3 | 13.8 | 18.7 | 24.7 | 20.3 | 20.2 | 30.0 | 27.5 | 20.2 | 22.5 | 18.7 | 22.3 | 22.3 |
| +180 | 24.7 | 20.2 | 17.8 | 22.3 | 19.5 | 26.2 | 16.5 | 18.3 | 16.7 | 22.7 | 20.7 | 15.5 | 21.3 | 18.2 | 19.7 | 16.7 |
| +240 | 19.5 | 17.2 | 22.7 | 17.0 | 19.7 | 19.5 | 25.2 | 15.2 | 19.5 | 21.2 | 21.3 | 19.7 | 19.3 | 13.7 | 23.7 | 20.8 |
| +300 | 25.2 | 24.2 | 21.7 | 19.0 | 20.0 | 20.3 | 15.3 | 15.8 | 19.2 | 24.2 | 26.5 | 24.2 | 25.3 | 22.2 | 23.5 | 18.2 |

[1]Water Load/Crossover Assay: All rabbits were water-loaded with 200 ml of water, p.o., just prior to receiving their ophthamlic drops. During study week one (Tables 1a and 2a), rabbits were randomly assigned to one of two treatment regimens: 4 rabbits (control) received vehicle in both eyes; another 4 (treated) received 0.5% HGP-2 fumarate in one eye and vehicle in the contralateral eye. Two days later crossover occurred: the original control rabbits received HGP-2 fumarate in one eye and vehicle in the other, while the original treated rabbits received vehicle in both eyes. On the second week of the study (refer to Tables 1b and 2b), animals were reassigned at random to treatment and the entire crossover procedure was repeated. This time, however, rabbits which received HGP-2 fumarate in their left eye during week 1 received HGP-2 fumarate in their right eye and vice versa.
[2]R = Right Eye, L = Left Eye.
[3]Time: Minutes post treatment; water-loading and administration of ophthalmic drops occurs at t = 0.
[4]Control: bilateral administration of vehicle.
[5]Treated: ♦ = unilateral administration of 0.5% HGP-2 fumarate. ★ = unilateral administration of vehicle.
[6]PT = Average of 2 pretreatment (baseline) IOP measurements.

TABLE 1b

INDIVIDUAL VALUES FOR ABSOLUTE INTRAOCULAR PRESSURE, STUDY WEEK 2
Effect of Unilateral Administration of HGP-2 Fumarate (0.5%, topical instillation of 50 ul drop)
on Absolute Intraocular Pressure in the Rabbit Using the Water Load/Crossover Assay[1]

Absolute Intraocular Pressure (mm Hg)
Rabbit No.

| Time[3] | C888 R[2] | C888 L[2] | C891 R | C891 L | C892 R | C892 L | C893 R | C893 L | C897 R | C897 L | C925 R | C925 L | C926 R | C926 L | C949 R | C949 L |
|---|---|---|---|---|---|---|---|---|---|---|---|---|---|---|---|---|
| | | | | | | | | Control[4] | | | | | | | | |
| PT[6] | 26.5 | 22.5 | 22.0 | 25.7 | 19.8 | 21.2 | 24.2 | 20.5 | 19.9 | 24.6 | 21.8 | 16.2 | 16.6 | 15.6 | 23.9 | 21.9 |
| +20 | 46.3 | 46.3 | 38.3 | 35.0 | 31.5 | 26.0 | 34.3 | 23.3 | 26.2 | 25.5 | 28.3 | 25.7 | 35.3 | 27.3 | 36.3 | 27.8 |
| +60 | 28.8 | 27.2 | 37.5 | 30.5 | 26.7 | 23.7 | 31.5 | 20.7 | 25.2 | 23.2 | 32.3 | 22.7 | 37.0 | 27.7 | 25.5 | 24.8 |
| +120 | 28.7 | 26.0 | 35.0 | 32.3 | 21.0 | 20.0 | 23.8 | 20.5 | 22.7 | 25.8 | 29.3 | 15.2 | 27.2 | 24.3 | 23.2 | 26.3 |
| +180 | 26.2 | 24.3 | 25.8 | 25.0 | 20.8 | 21.7 | 24.7 | 24.3 | 20.0 | 27.0 | 20.8 | 13.7 | 25.0 | 21.8 | 22.8 | 21.7 |
| +240 | 31.3 | 22.3 | 29.5 | 28.2 | 21.5 | 21.5 | 23.5 | 22.5 | 22.7 | 24.0 | 18.0 | 16.3 | 23.7 | 13.0 | 19.2 | 22.7 |
| +300 | 28.0 | 26.7 | 19.8 | 19.8 | 24.0 | 18.5 | 30.3 | 20.8 | 29.2 | 21.3 | 24.3 | 19.2 | 19.2 | 23.0 | 27.0 | 22.7 |
| | | | | | | | | Treated[5] | | | | | | | | |
| | ♦ | ★ | ★ | ♦ | ★ | ♦ | ★ | ♦ | ★ | ♦ | ♦ | ★ | ♦ | ★ | ♦ | ★ |
| PT[6] | 25.9 | 23.7 | 25.0 | 20.6 | 24.9 | 20.7 | 24.0 | 14.6 | 17.1 | 19.7 | 22.3 | 17.4 | 24.5 | 22.0 | 27.7 | 22.0 |
| +20 | 45.0 | 46.3 | 27.0 | 32.8 | 23.5 | 25.8 | 39.8 | 36.8 | 31.2 | 32.0 | 32.3 | 25.7 | 40.5 | 35.3 | 43.7 | 36.7 |
| +60 | 39.0 | 37.8 | 37.2 | 26.5 | 24.8 | 21.3 | 30.0 | 22.2 | 25.5 | 20.3 | 28.5 | 21.2 | 31.0 | 28.5 | 33.3 | 24.8 |
| +120 | 24.5 | 24.5 | 31.2 | 17.0 | 24.3 | 22.0 | 23.3 | 19.5 | 21.2 | 19.7 | 26.3 | 27.7 | 18.7 | 22.0 | 25.2 | 19.3 |
| +180 | 22.2 | 25.3 | 30.3 | 21.0 | 20.3 | 18.5 | 24.0 | 15.0 | 19.3 | 21.0 | 20.8 | 19.2 | 24.5 | 27.7 | 27.8 | 19.3 |
| +240 | 27.0 | 22.7 | 23.2 | 18.2 | 20.8 | 36.2 | 25.2 | 23.7 | 22.5 | 20.8 | 25.8 | 16.3 | 20.0 | 18.7 | 21.3 | 21.3 |
| +300 | 27.2 | 19.0 | 20.8 | 17.5 | 25.5 | 19.3 | 21.3 | 14.8 | 15.0 | 23.0 | 21.8 | 17.3 | 19.7 | 19.3 | 22.5 | 21.5 |

[1]Water Load/Crossover Assay: All rabbits were water loaded with 200 ml of water, p.o., just prior to receiving their ophthamlic drops. During study week 1 (Tables 1a and 2a), rabbits were randomly assigned to one of two treatment regimens: 4 rabbits (control) received vehicle in both eyes; another 4 (treated) received 0.5% HGP-2 fumarate in one eye and vehicle in the contralateral eye. Two days later crossover occurred: the original control rabbits received HGP-2 fumarate in one eye and vehicle in the other, while the original treated rabbits received vehicle in both eyes. On the second week of the study (Tables 1b and 2b), animals were reassigned at random to treatment and the entire crossover procedure was repeated. This time, however, rabbits which received HGP-2 fumarate in their left eye during week 1 received HGP-2 fumarate in their right eye, and vice versa.
[2]R = Right Eye; L = Left Eye.
[3]Time: Minutes post treatment; water-loading and administration of ophthalmic drops occurs at t = 0.
[4]Control: bilateral administration of vehicle.
[5]Treated: ♦ = unilateral administration of 0.5% HGP-2 fumarate. ★ = unilateral administration of vehicle.
[6]PT = Average of 2 pretreatment (baseline) IOP measurements.

TABLE 2a

INDIVIDUAL VALUES FOR RELATIVE INTRAOCULAR PRESSURE, STUDY WEEK 1
Effect of Unilateral Administration of HGP-2 Fumarate (0.5%, topical instillation of 50 ul drop)
on Relative Intraocular Pressure in the Rabbit Using the Water Load/Crossover Assay[1]

Relative Intraocular Pressure (mm Hg)[2]
Rabbit No.

| Time[4] | C888 R[3] | C888 L[3] | C891 R | C891 L | C892 R | C892 L | C893 R | C893 L | C897 R | C897 L | C925 R | C925 L | C926 R | C926 L | C949 R | C949 L |
|---|---|---|---|---|---|---|---|---|---|---|---|---|---|---|---|---|
| | | | | | | | | Control[5] | | | | | | | | |
| +20 | +9.4 | +11.0 | +4.6 | +12.2 | +14.0 | +7.4 | +4.8 | +12.5 | +13.8 | +13.3 | +15.1 | +15.2 | +9.5 | +5.8 | +10.5 | +11.8 |
| +60 | −4.1 | +2.8 | +16.0 | +20.9 | +10.9 | +9.9 | +7.1 | +4.5 | +4.8 | +8.1 | +3.1 | +6.4 | +9.0 | +8.4 | +6.0 | +5.5 |
| +120 | −6.6 | +1.7 | +4.0 | +7.0 | +0.7 | +0.3 | −6.7 | −4.8 | +6.0 | +3.5 | +1.6 | +1.7 | −0.5 | +0.3 | +2.6 | −1.0 |
| +180 | −11.8 | −7.2 | −2.0 | −0.1 | +0.2 | −0.2 | −7.6 | +0.5 | +4.0 | +1.0 | +2.0 | +0.2 | −3.8 | −4.1 | −3.7 | −2.8 |
| +240 | −2.1 | −7.3 | +9.0 | +6.7 | +1.4 | −1.1 | +2.4 | +4.2 | −0.7 | +2.5 | +4.0 | +2.9 | +3.7 | −8.7 | 0.0 | +1.1 |
| +300 | −5.6 | −6.2 | +7.1 | +4.0 | +1.7 | −0.7 | −4.7 | +2.5 | +1.6 | +1.3 | +3.8 | +1.2 | −1.2 | −8.6 | +1.6 | +5.3 |
| | | | | | | | | Treated[6] | | | | | | | | |
| +20 | ★+7.9 | ♦+10.6 | ♦+4.4 | ★+6.3 | ♦+11.8 | ★+8.2 | ♦+15.8 | ★+10.9 | ♦+8.1 | ★+0.7 | ★+20.0 | ♦+15.6 | ★+11.9 | ♦+12.5 | ★+17.9 | ♦+17.7 |
| +60 | +2.5 | +0.7 | +4.4 | +9.2 | +3.8 | +9.5 | +4.5 | +6.1 | −0.1 | +2.2 | +6.9 | +4.6 | +11.1 | +1.8 | +1.4 | +4.6 |
| +120 | −15.1 | −8.1 | −3.3 | +4.3 | −5.2 | −0.6 | −0.5 | +3.2 | −1.2 | +8.2 | +8.7 | +1.1 | −2.4 | −4.0 | −1.1 | +1.7 |
| +180 | −6.1 | −3.9 | −9.3 | +2.7 | +0.5 | +6.9 | −8.7 | +1.2 | −4.7 | +0.9 | +1.9 | −3.6 | −3.6 | −4.5 | −3.7 | −3.9 |
| +240 | −11.3 | −6.9 | −4.4 | −8.0 | +0.7 | +0.4 | 0.0 | −1.9 | −1.9 | −0.6 | +2.5 | +0.6 | −5.6 | −9.0 | +0.3 | +0.2 |
| +300 | −0.1 | +0.1 | −5.4 | −6.0 | +1.0 | +1.0 | −9.9 | −1.3 | −1.3 | +2.4 | +7.7 | +5.1 | +0.4 | −0.5 | +0.1 | −2.4 |

[1]Water Load/Crossover Assay: All rabbits were water-loaded with 200 ml of water, p.o., just prior to receiving their ophthalmic drops. During study week one (Tables 1a and 2a), rabbits were randomly assigned to one of two treatment regimens: 4 rabbits (control) received vehicle in both eyes; another 4 (treated) received 0.5% HGP-2 fumarate in one eye and vehicle in the contralateral eye. Two days later crossover occurred: the original control rabbits received HGP-2 fumarate in one eye and vehicle in the other, while the original treated rabbits received vehicle in both eyes. On the second week of the study (refer to Tables 1b and 2b), animals were reassigned at random to treatment and the entire crossover procedure was repeated. This time, however, rabbits which received HGP-2 fumarate in their left eye during week 1 received HGP-2 fumarate in their right eye and vice versa.
[2]Relative Intraocular Pressure (mm Hg): IOP (pretreatment) + IOP (time 0); a post treatment pressure drop is (−), a rise is (+). Refer to Table 1a for absolute pressure values.
[3]R = Right Eye, L = Left Eye.
[4]Time: Minutes post treatment; water-loading and administration of ophthalmic drops occurs at t = 0.
[5]Control: bilateral administration of vehicle.
[6]Treated: ♦ = unilateral administration of 0.5% HGP-2 fumarate. ★ = unilateral administration of vehicle.

TABLE 2b

INDIVIDUAL VALUES FOR RELATIVE INTRAOCULAR PRESSURE, STUDY WEEK 2
Effect of Unilateral Administration of HGP-2 Fumarate (0.5%, topical instillation of 50 ul drop) on Relative Intraocular Pressure in the Rabbit Using the Water Load/Crossover Assay[1]

Relative Intraocular Pressure (mm Hg)[2]
Rabbit No.

| Time[4] | C888 R[3] | C888 L[3] | C891 R | C891 L | C892 R | C892 L | C893 R | C893 L | C897 R | C897 L | C925 R | C925 L | C926 R | C926 L | C949 R | C949 L |
|---|---|---|---|---|---|---|---|---|---|---|---|---|---|---|---|---|
| | | | | | | | | Control[5] | | | | | | | | |
| +20 | +19.8 | +23.8 | +16.3 | +9.3 | +11.7 | +4.8 | +10.1 | +2.8 | +6.3 | +0.9 | +6.5 | +9.5 | +18.7 | +11.7 | +12.4 | +5.9 |
| +60 | +2.3 | +4.7 | +15.5 | +4.8 | +6.9 | +2.5 | +7.3 | +0.2 | +5.3 | −1.4 | +10.5 | +6.5 | +20.4 | +12.1 | +1.6 | +2.9 |
| +120 | +2.2 | +3.5 | +13.0 | +6.6 | +1.2 | −1.2 | −0.4 | 0.0 | +2.8 | +1.2 | +7.5 | −1.0 | +10.6 | +8.7 | −0.7 | +4.4 |
| +180 | −0.3 | +1.8 | +3.8 | −0.7 | +1.0 | −0.5 | +0.5 | +3.8 | +0.1 | +2.4 | −1.0 | −2.5 | +8.4 | +6.2 | −1.1 | −0.2 |
| +240 | +4.8 | −0.2 | +7.5 | +2.5 | +1.7 | +0.3 | −0.7 | +2.0 | +2.8 | −0.6 | −3.8 | +0.1 | +7.1 | −2.6 | −4.7 | −0.8 |
| +300 | +1.5 | +4.2 | −2.2 | −5.9 | +4.2 | −2.7 | +6.1 | +0.3 | +9.3 | −3.3 | +2.5 | +3.0 | +2.6 | +7.4 | +3.1 | +0.8 |
| | | | | | | | | Treated[6] | | | | | | | | |
| +20 | ◆ +19.1 | ★ +22.6 | ★ +2.0 | ◆ +12.2 | ★ −1.4 | ◆ +5.1 | ★ +15.8 | ◆ +22.2 | ★ +14.1 | ◆ +12.3 | ◆ +10.0 | ★ +8.3 | ◆ +16.0 | ★ +13.3 | ◆ +16.0 | ★ +14.7 |
| +60 | +13.1 | +14.1 | +12.2 | +5.9 | −0.1 | +0.6 | +6.0 | +7.6 | +8.4 | +0.6 | +6.2 | +3.8 | +6.5 | +6.5 | +5.6 | +2.8 |
| +120 | −1.4 | +0.8 | +6.2 | −3.6 | −0.6 | +1.3 | +0.7 | +4.9 | +4.1 | 0.0 | +4.0 | +10.3 | −5.8 | 0.0 | −2.5 | −2.7 |
| +180 | −3.7 | +1.6 | +5.3 | +0.4 | −4.6 | −2.2 | 0.0 | +0.4 | +2.2 | +1.3 | −1.5 | +1.8 | 0.0 | +5.7 | +0.1 | −2.7 |
| +240 | +1.1 | −1.0 | −1.8 | −2.4 | −4.1 | +15.5 | +1.3 | +9.1 | +5.4 | +1.1 | +3.5 | −1.1 | −4.5 | −3.3 | −6.4 | −0.7 |
| +300 | +1.3 | −4.7 | −4.2 | −3.1 | +0.6 | −1.4 | −2.7 | +0.2 | −2.1 | +3.3 | −0.5 | −0.1 | −4.8 | −2.7 | −5.2 | −0.5 |

[1]Water Load/Crossover Assay: All rabbits were water-loaded with 200 ml of water, p.o., just prior to receiving their ophthalmic drops. During study week one (Tables 1a and 2a), rabbits were randomly assigned to one of two treatment regimens: 4 rabbits (control) received vehicle in both eyes; another 4 (treated) received 0.5% HGP-2 fumarate in one eye and vehicle in the contralateral eye. Two days later crossover occurred: the original control rabbits received HGP-2 fumarate in one eye and vehicle in the other, while the original treated rabbits received vehicle in both eyes. On the second week of the study (refer to Tables 1b and 2b), animals were reassigned at random to treatment and the entire crossover procedure was repeated. This time, however, rabbits which received HGP-2 fumarate in their left eye during week 1 received HGP-2 fumarate in their right eye and vice versa.
[2]Relative Intraocular Pressure (mm Hg): IOP (pretreatment) + IOP (time t); a post treatment pressure drop is (−), a rise is (+). Refer to Table 1a for absolute pressure values.
[3]R = Right Eye, L = Left Eye.
[4]Time: Minutes post treatment; water-loading and administration of ophthalmic drops occurs at t = 0.
[5]Control: bilateral administration of vehicle.
[6]Treated: ◆ = bilateral administration of 0.5% HGP-2 fumarate. ★= unilateral administration of vehicle.

TABLE 3

EVALUATION FOR CONTRALATERAL EYE EFFECT IN WATER-LOADED RABBITS RECEIVING A SINGLE UNILATERAL DOSE OF 0.5% HGP-2 FUMARATE: HGP-2 FUMARATE TREATED EYE VS. CONTRALATERAL EYE INTRAOCULAR PRESSURE (IOP) RESULTS

| | MEAN INTRAOCULAR PRESSURE (S.E.)[1] in mm of Hg | |
|---|---|---|
| | HGP-2 FUMARATE[2] | CONTRALATERAL EYE[3] |
| ABSOLUTE IOP | | |
| Pretreatment | 22.2 (0.9) | 22.3 (0.9) |
| +20 Minutes | 35.3 (1.3) | 33.2 (1.8) |
| +60 | 26.6 (1.3) | 28.7 (1.3) |
| +120 | 20.8 (0.9)[a] | 23.7 (1.1)[a] |
| +180 | 19.5 (0.9)[b] | 22.6 (0.9)[b] |
| +240 | 22.0 (1.3) | 20.5 (0.7) |
| +300 | 20.7 (0.8) | 21.2 (0.9) |
| RELATIVE IOP | | |
| +20 Minutes | 13.1 (1.2) | 10.8 (1.7) |
| +60 | 4.4 (0.8) | 6.4 (1.0) |
| +120 | −1.4 (0.9)[a] | 1.5 (1.5)[a] |
| +180 | −2.7 (0.8)[c] | 0.6 (1.0)[c] |
| +240 | −0.2 (1.5) | −1.8 (1.0) |
| +300 | −1.5 (0.9) | −0.8 (0.8) |

Notes:
[1] Mean of 16 values (standard error of the mean), refer to Tables 1a, 1b, 2a and 2b above for individual values.
[2] HGP-2 fumarate treated eye: treated with one 50 ul drop of 0.5% HGP-2 fumarate (opposite eye received vehicle only).
[3] Contralateral Eye: treated with vehicle only (opposite eye received one 50 ul drop of HGP-2 fumarate).
[a] Significantly different: $0.025 < p < 0.05$
[b] Significantly different: $0.01 < p < 0.025$
[c] Significantly different: $0.005 < p < 0.01$

TABLE 4

EVALUATION FOR HYPOTENSIVE ACTIVITY OF A SINGLE UNILATERAL DOSE OF 0.5% FUMARATE: HGP-2 FUMARATE TREATED EYE VS. CROSSOVER CONTROL EYE INTRAOCULAR PRESSURE (IOP) RESULTS.

| | MEAN INTRAOCULAR PRESSURE (S.E.)[1] in mm of Hg | |
|---|---|---|
| | HGP-2 FUMARATE[2] | CROSSOVER CONTROL[3] |
| ABSOLUTE IOP | | |
| Pretreatment | 22.2 (0.9) | 22.0 (0.9) |
| +20 Minutes | 35.3 (1.3)[b] | 31.8 (1.4)[b] |
| +60 | 26.6 (1.3) | 28.4 (1.4) |
| +120 | 20.8 (0.9)[a] | 24.1 (1.1)[a] |
| +180 | 19.5 (0.9)[b] | 21.6 (0.9)[b] |
| +240 | 22.0 (1.3) | 22.5 (1.5) |
| +300 | 20.7 (0.8) | 21.7 (1.2) |
| RELATIVE IOP | | |
| +20 Minutes | 13.1 (1.2)[a] | 9.8 (0.4)[a] |
| +60 | 4.4 (0.8) | 6.4 (1.4) |
| +120 | −1.4 (0.9)[a] | 2.1 (1.0)[a] |
| +180 | −2.7 (0.8)[a] | −0.5 (1.0)[a] |
| +240 | −0.2 (1.5) | 0.5 (1.2) |
| +300 | −1.5 (0.9) | −0.3 (1.1) |

Notes:
[1] Mean of 16 values (standard error of the mean), refer to Tables 1a, 1b, 2a and 2b above for individual values.
[2] HGP-2 fumarate treated eye: treated with one 50 ul drop of 0.5% HGP-2 fumarate (opposite eye received vehicle only).
[3] Crossover control eye: treated with vehicle only (opposite eye simultaneously received vehicle), crossover eye for treated eye.
[a] Significantly different: $0.025 < p < 0.05$
[b] Significantly different: $0.01 < p < 0.025$ The invention has been described in detail with reference to the preferred embodiments thereof. However, it will be appreciated that those skilled in the art, upon consideration of this disclosure, may make modifications and improvements within the spirit and scope of the invention.

What is claimed is:

1. A method of treating glaucoma comprising administering to a mammal suffering from or susceptible to glaucoma about 0.01 to 10 mg a fumarate salt of 4-(diethyl-3-(1-methyloctyl)-7,8,9,10-tetrahydro-6,6,9-trimethyl-6H-dibenzo[b,d]pyran-1-ol, 4-diethylamino)butyric acid ester.

2. The method of claim 1 wherein the fumarate salt is administered orally.

3. The method of claim 1 wherein the fumarate salt is administered topically.

4. The method of claim 1 wherein the fumarate salt is administered by means of a transdermal patch.

5. The method of claim 1 wherein from about 0.01 to 5 mg of the fumarate salt is administered per unit dose.

6. The method of claim 1 wherein from about 0.1 to 5 mg of the fumarate salt is administered per unit dose.

7. The method of claim 1 wherein the mammal is a human.

8. The method of claim 2 wherein the mammal is a human.

9. The method of claim 3 wherein the mammal is a human.

10. The method of claim 4 wherein the mammal is a human.

11. The method of claim 5 wherein the mammal is a human.

12. The method of claim 6 wherein the mammal is a human.

13. The method of claim 1 wherein the fumarate salt is administered as a powder or granules.

14. The method of claim 13 wherein the mammal is a human.

* * * * *